United States Patent [19]

Buschmann et al.

[11] 4,301,284

[45] Nov. 17, 1981

[54] N-(3-TERTBUTYL-CHLOROPHENYL-2-METHYL-1-PROPYL)-2,6-DIMETHYL MORPHOLINES

[75] Inventors: Ernst Buschmann; Bernd Zeeh, both of Ludwigshafen; Ernst-Heinrich Pommer, Limburgerhof; Norbert Goetz, Worms, all of Fed. Rep. of Germany

[73] Assignee: BASF Aktiengesellschaft, Fed. Rep. of Germany

[21] Appl. No.: 40,222

[22] Filed: May 18, 1979

[30] Foreign Application Priority Data

Jul. 8, 1978 [DE] Fed. Rep. of Germany ....... 2830127

[51] Int. Cl.³ ............................................ C07D 265/30
[52] U.S. Cl. .................................... 544/106; 544/174; 544/177; 544/178
[58] Field of Search ................ 544/106, 178, 174, 177

[56] References Cited

U.S. PATENT DOCUMENTS

| | | | |
|---|---|---|---|
| 3,574,841 | 4/1971 | Driscoll | 424/248.4 |
| 3,639,476 | 2/1972 | Eberle et al. | 544/106 |
| 3,686,399 | 8/1972 | Sanne et al. | 424/248 |
| 3,824,312 | 7/1974 | Seidel | 424/248.4 |
| 4,202,894 | 5/1980 | Pfiffner | 544/173 |

FOREIGN PATENT DOCUMENTS

| | | | |
|---|---|---|---|
| 70660 | 1/1976 | Australia | 544/106 |
| 1137733 | 10/1962 | Fed. Rep. of Germany | 544/106 |
| 2752135 | 5/1978 | Fed. Rep. of Germany 4n . | |
| 2656747 | 6/1978 | Fed. Rep. of Germany . | |

*Primary Examiner*—Henry R. Jiles
*Assistant Examiner*—R. W. Ramsuer
*Attorney, Agent, or Firm*—Keil & Witherspoon

[57] ABSTRACT

New N-arylpropyl-substituted amines, and salts, molecular compounds and adducts thereof, having a good fungicidal action, fungicides containing these compounds, and processes for manufacturing these compounds.

2 Claims, No Drawings

N-(3-TERTBUTYL-CHLOROPHENYL-2-METHYL-1-PROPYL)-2,6-DIMETHYL MORPHOLINES

The present invention relates to new and valuable N-arylpropyl-substituted amines, and salts, molecular compounds and adducts thereof, having a good fungicidal action, fungicides containing these compounds, and processes for manufacturing these compounds.

The use of N-tridecyl-2,6-dimethylmorpholine, its salts, and its molecular compounds and adducts, as fungicides has been disclosed (German Pat. No. 1,164,152, German 1,173,722, German Laid-Open Application DE-OS No. 2,461,513). However, its fungicidal action and its compatibility with crop plants do not meet all the requirements of agricultural practice.

We have found that N-arylpropyl-substituted cyclic amines of the formula

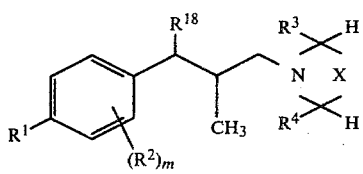

where $R^1$ is teriary alkyl, tertiary cycloalkyl, or haloalkyl with 1 to 3 halogens, $R^2$ is alkyl of 1 to 3 carbon atoms, chlorine, bromine, fluorine, or alkoxy, m denotes one of the integers 0, 1, 2 and 3, $R^1$ denoting, where m=0, haloalkyl with 1 to 3 halogens, $R^3$ and $R^4$ are identical or different and each denotes hydrogen or lower alkyl, X denotes

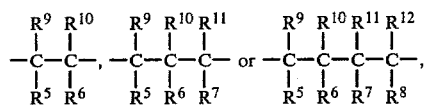

$R^5$ to $R^{12}$ being identical or different and each denoting hydrogen, lower alkyl, hydroxy, -CH$_2$OH or phenyl, X further denotes

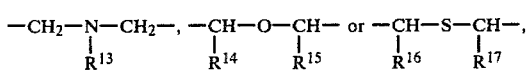

$R^{13}$ to $R^{17}$ being identical or different and each denoting hydrogen or lower alkyl, further, when one of $R^5$ to $R^{12}$ and $R^{14}$ to $R^{17}$ denotes alkyl, it may be simultaneously linked with two different carbon atoms to form an alkylene bridge, and further, two of $R^5$ to $R^{12}$ and $R^{14}$ to $R^{17}$ may together form a carbon chain in the form of a fused cycloalkyl ring or aromatic ring, and $R^{18}$ denotes hydrogen or alkoxy, and salts, molecular compounds and adducts thereof, have a fungicidal action superior to that of prior art morpholine derivatives.

Examples of salts are those with inorganic acids, e.g., chlorides, fluorides, bromides, iodides, sulfates, nitrates, phosphates, acetates and propionates. Molecular compounds and adducts are formed for instance with acids of surfactants, e.g., dodecylbenzenesulfonic acid.

If the new compounds are 2,6-dimethylmorpholines or 3,5-dimethylpiperidines, they may be isolated as cis and trans isomers.

The new compounds are prepared by reacting a halide of the formula

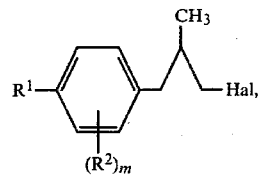

where $R^1$, $R^2$ and m have the above meanings and Hal denotes chloro or bromo, with a compound of the formula

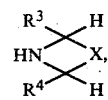

where $R^3$, $R^4$ and X have the above meanings.

The reaction is carried out for instance in fairly high-boiling solvents, or in the absence of solvents, at from 80° and 200° C. The reaction is preferably carried out without solvents at from 100° to 160° C.

The halides according to formula II are obtained by alkylation of phenylpropyl halides of the formula

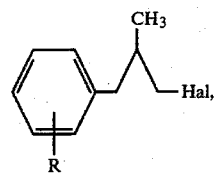

where R denotes hydrogen, alkyl of 1 to 3 carbon atoms, alkoxy or fluoro, and Hal denotes bromo or chloro, with an olefin, alcohol or alkyl halide in the presence of an acid catalyst, followed, if desired, by reaction with chlorine or bromine.

For example, the reaction of 2-methyl-3-phenylpropyl chloride with 2-methallyl chloride in the presence of concentrated sulfuric acid gives 3-[p-(1-chloromethyl-1-methylethyl)]-phenyl-2-methylpropyl chloride, as described below.

Preparation of 3-[p-(1-chloromethyl-1-methylethyl)]-phenyl-2-methylpropyl chloride At 10° C., 9 parts by weight of 2-methallyl chloride is dripped into a mixture of 17 parts by weight of 2-methyl-3-phenylpropyl chloride and 10 parts by weight of 96% strength sulfuric acid. The mixture is stirred for 14 hours at room temperature (20° C.), and the crude product is dissolved in CHCl$_3$, washed with water, dried over Na$_2$CO$_3$, and distilled. There is obtained 14 parts by weight of 3-[p-(chloromethyl-1-methylethyl)]-phenyl-2-methylpropyl chloride; b.p. (0.1 mm) 129°–131° C. Yield: 54% (based on 2-methyl-3-phenylpropyl chloride).

Compounds of the formula

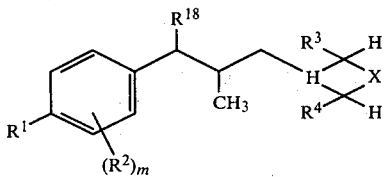

where $R^1$, $R^2$, $R^3$, $R^4$ and m have the above meanings and $R^{18}$ is alkoxy, are prepared by reactions known in the art, in accordance with the following scheme:

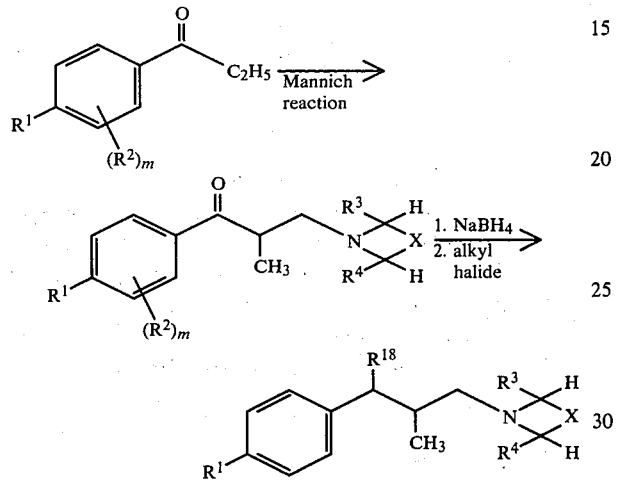

The following examples illustrate the preparation of the new compounds.

EXAMPLE 1

A mixture of 24 g of 3-(p-1-chloromethyl-1-methylethylphenyl)-2-methylpropyl chloride and 32 g of cis-2,6-dimethylmorpholine is heated for 4 hours at 150° C. The crude product is dissolved in chloroform, washed several times with water, and dried over $Na_2SO_4$, the solvent is evaporated and the residue is distilled. There is obtained 21 g of N-[3-(p-1-chloromethyl-1-methylethylphenyl)-2-methylpropyl]-2,6-cis-dimethylmorpholine (active ingredient no. 1); b.p. (0.1 mm) 165°–166° C.

EXAMPLE 2

A solution of 23 g of 2,6-cis-dimethylmorpholine and 30.4 g of 3-(p-tert-butyl-o-chlorophenyl)-2-methylpropyl bromide in 150 ml of acetonitrile is refluxed for 4 hours. The crude product is dissolved in methylene chloride, the solution is washed with water, aqueous sodium bicarbonate solution and again with water, and dried over $Na_2SO_4$, the solvent is evaporated and the residue is distilled. There is obtained 22 g of N-[3-(p-tert-butyl-o-chlorophenyl)-2-methylpropyl]-2,6-cis-dimethylmorpholine (active ingredient no. 2); b.p. (0.05 mm) 133°–135° C.

The following active ingredients are obtained analogously:

| Active ingredient no. | |
|---|---|
| 3 | N-[3-p-tert-butyl-o-bromophenyl)-2-methylpropyl]-2,6-cis-dimethylmorpholine, b.p. (0.05 mm) = 145°–147° C. |
| 4. | N-[3-(p-tert-butyl-o-bromophenyl)-2-methylpropyl]-3,5-di-methylpiperidine, b.p. (0.2 mm) = 154°–165° C. |
| 5 | N-[3-(p-tert-amyl-o-bromophenyl)-2-methylpropyl]-2,6-cis-dimethylmorpholine, b.p. (0.2 mm) = 183°–187° C. |
| 6 | N-[3-(o-tert-butyl-p-methoxyphenyl)-2-methylpropyl]-2,6-cis-dimethylmorpholine and N-[3-(m-tert-butyl-p-methoxyphenyl)-2-methylpropyl]-2,6-cis-dimethylmorpholine, b.p. (0.1 mm) = 160° C. |
| 7 | N-[3-(tert-butyl-o-methylphenyl)-2-methylpropyl]-2,6-cis-dimethylmorpholine, b.p. (0.1 mm) = 160° C. |
| 8 | (3-p-tert-butylphenyl-3-methoxy-2-methylpropyl)-2,6-cis-dimethylmorpholine, b.p. (0.1 mm) = 158°–160° C. |
| 9 | N-[3-(tert-butyl-o-methylphenyl)-2-methylpropyl]-2,6-cis-dimethylmorpholine hydrochloride, m.p. 178°–179° C. (decomposes) |
| 10 | N-[3-(p-tert-butyl-o-chlorophenyl)-2-methylpropyl]-2,6-cis-dimethylmorpholine hydrochloride, m.p. 240°–242° C. (decomposes) |
| 11 | N-[3-(p-tert-butyl-o-bromophenyl)-2-methylpropyl]-2,6-cis-dimethylmorpholine hydrochloride, m.p. 244°–246° C. (decomposes) |
| 12 | N-[3-(p-1-chloromethyl-1-methylethylphenyl)-2-methylpropyl]-2,5-dimethylpyrrolidine, b.p. (0.2 mm) = 168°–172° C. |
| 13 | N-[3-(p-1-chloromethyl-1-methylethylphenyl)-2-methylpropyl]-3-methylpiperidine, b.p. (0.1 mm) = 165°–169° C. |
| 14 | N[3-(p-1-chloromethyl-1-methylethylphenyl)-2-methylpropyl]-3-methylpiperidine hydrochloride, m.p. 148°–150° C. |
| 15 | N-(3-p-tert-butylphenyl-3-methoxy-2-methylpropyl)-2,6-di-methylmorpholine, b.p. (0.2 mm) = 132°–137° C. |
| 16 | N-[3-(p-1-chloromethyl-1-methylethylphenyl)-2-methylpropyl]-3,5-dimethylpiperidine, b.p. (0.1 mm) = 173°–176° C. |
| 17 | N-[3-(p-1-chloromethyl-1-methylethylphenyl)-2-methylpropyl]-3,5-dimethylpiperidine hydrochloride, m.p. 217°–219° C. (decomposes) |
| 18 | (3-p-tert-amyl-o-chlorophenyl-2-methylpropyl)-3,5-di-methylpiperidine and N-(3-p-tert-amyl-m-chlorophenyl-2-methyipropyl)-3,5-dimethylpiperidine, b.p. (0.1 mm) 167°–169° C. |
| 19 | mixture of N-(3-p-tert-amyl-o-chlorophenyl-2-methylpropyl-3,5-dimethylpiperidine hydrochloride and N-(3-p-tert-amyl-m-chlorophenyl-2-methylpropyl)-3,5-dimethylpiperidine hydrochloride, m.p. 190°–191° C. |
| 20 | mixture of N-(3-p-tert-amyl-o-chlorophenyl-2-methylpropyl)-2,6-cis-dimethylmorpholine and N-(3-p-tert-amyl-m-chlorophenyl-2-methylpropyl)-2,6-cis-dimethylmorpholine, b.p. (0.1 mm) = 152°–160° C. |
| 21 | N-[3-(p-1-chloromethyl-1-methylethylphenyl)-2-methylpropyl]-2,6-dimethylthiamorpholine, b.p. (0.1 mm) = 188°–190° C. |
| 22 | N[3-(p-1-chloromethyl-1-methylethylphenyl)-2-methylpropyl]-2,6-dimethyl-thiamorpholine hydrochloride, m.p. = 139°–141° C. |
| 23 | N-[3-(p-1-chloromethyl-1-methylethylphenyl)-2-methylpropyl]-4-methylpiperidine, b.p. (0.1 mm) = 170°–176° C. |
| 24 | N-[3-(p-1-chloromethyl-1-methylphenyl)-2-methylpropyl]-4-methylpiperidine hydrochloride, m.p. 167°–170° C. |
| 25 | N-[3-(p-1-chloromethyl-1-methylethylphenyl)-2-methylpropoxy]-piperidine, b.p. (0.1 mm) = 150° C. |
| 26 | N-[3-(p-1-chloromethyl-1-methylethylphenyl)-2-methylpropyl]-piperidine hydrochloride, m.p. 156°–158° C. |

-continued

| Active ingredient no. | |
|---|---|
| 27 | N-(3-m-tert-butyl-o-methoxyphenyl-2-methylpropyl)-2,6-cis-dimethylmorpholine, b.p. (0.1 mm) = 150°–154° C. |
| 28 | N-[3-(p-1-chloromethyl-1-methylethylphenyl)-2-methylpropyl]-isoquinoline, b.p. (0.1 mm) = 190°–192° C. |
| 29 | N[-3-(p-1-chloromethyl-1-methylethylphenyl)-2-methylpropyl]-isoquinolines hydrochloride, m.p. 189°–190° C. |
| 30 | N-[3-(p-1-chloromethyl-1-methylethylphenyl)-2-methylpropyl]-3,3-dimethylpiperidine, b.p. (0.1 mm) = 170°–174° C. |
| | N-[3-(p-1-chloromethyl-1-methylethylphenyl)-2-methylpropyl]-3,3-dimethylpiperidine, m.p. 166°–168° C. |
| 32 | 1-[3-(p-1-chloromethyl-1-methylethylphenyl)-2-methylpropyl]-4-methylpiperazine, b.p. (0.1 mm) = 160°–161° C. |
| 33 | 1-[3-(p-1-chloromethyl-1-methylethylphenyl)-2-methylpropyl]-4-methylpiperazine hydrochloride, m.p. 202°–204° C. |
| 34 | N-[3-(p-tert-butyl-o-chlorophenyl)-2-methylpropyl]-piperidine b.p. (0.1 mm) = 122°–128° C. |
| 35 | N-[3-(p-tert-butyl-o-chlorophenyl)-2-methylpropyl]-3-methylpiperidine, b.p. (0.2 mm) = 143°–146° C. |
| 36 | N-[3-(p-tert-butyl-o-chlorophenyl)-2-methylpropyl]-4-methylpiperidine, b.p. (0.1 mm) = 141°–143° C. |
| 37 | N-[3-(p-tert-butyl-o-chlorophenyl)-2-methylpropyl] 3,5-dimethylpiperidine, b.p. (0.1 mm) = 141°–143° C. |
| 38 | N-[3-(p-tert-butyl-o-chlorophenyl)-2-methylpropyl]-hexamethylenimine, b.p. (0.2 mm) = 150°–154° C. |
| 39 | N-[3-(p-tert-butyl-o-chlorophenyl)-2-methylpropyl]-4-tert-butylhexamethylenimine, b.p. (0.1 mm) = 171°–175° C. |
| 40 | N-[3-(p-tert-butyl-o-chlorophenyl)-2-methylpropyl]-3,5-di-ethylmorpholine. |

The active ingredients according to the invention and fungicides containing them are particularly suitable for combating plant diseases, e.g., *Erysiphe graminis* in cereals, *Erysiphe cichoriacearum* in Cucurbitaceae, *Podosphaera leucotricha* in apples, *Uncinula necator* in roses, *Microsphaera querci* in oaks, *Botrytis cinerea* in strawberries and grapes, *Micosphaerella musicola* in bananas, Puccinia species in beans, *Hemileia vastatrix* in coffee, and *Rhizoctonia solani*. The active ingredients have a systemic action; they are taken up not only through the roots but also via the foliage, and translocated in the plant tissue.

When the new active ingredients are used to treat plants against fungus infections, application rates are from 0.01 to 4 kg of active ingredient per hectare. For the surface protection of trees or fruit, the active ingredients may also be used in conjunction with plastics dispersions in amounts of from 0.25 to 5%, based on the weight of the dispersion.

The fungicides generally contain from 0.1 to 95, and preferably from 0.5 to 90, wt% of active ingredient. Application is effected for instance by pouring, spraying, dusting, powdering, painting, or impregnating.

The active ingredients may also be mixed with other, prior art, fungicides. In many cases, the spectrum of fungicidal action is increased; with a number of these fungicidal compositions in the weight ratio range of from 1:10 to 10:1, synergistic effects also occur, i.e., the fungicidal action of the combination product is greater than the effect of the individual components added together.

Examples of fungicides which may be combined with the compounds according to the invention are: dithiocarbamates and their derivatives, e.g., zinc dimethyldithiocarbamate, manganese N,N-ethylene-bis-dithiocarbamate, manganese zinc N,N-ethylenediamine-bis-dithiocarbamate, zinc N,N-ethylene-bis-dithiocarbamate, tetramethylthiuram disulfide, the ammonia complex of zinc N,N-ethylene-bis-dithiocarbamate and N,N'-polyethylene- bis (thiocarbamoyl)-disulfide, zinc N,N'-propylene-bis-dithiocarbamate, and the ammonia complex of zinc N,N'-propylene-bis-dithiocarbamate and N-N'-polypropylene-bis-(thiocarbamoyl)-disulfide; heterocyclic compounds, e.g. N-trichloromethylthiotetrahydrophthalimide, N-trichloromethylthio-phthalimide, N-(1,1,2,2-tetrachloroethylthio)-tetrahydrophthalimide, methyl 1-(butylcarbamoyl)-2-benzimidazole carbamate, 2-methyloxycarbonylaminobenzimidazole, 2,3-dihydro-5-carboxanilido-6-methyl-1,4-oxathiine-4,4-dioxide, 2,3-dihydro-5-carboxanilido-6-methyl-1,4-oxathiine, 5-butyl-2-dimethylamino-4-hydroxy-6-methyl-pyrimidine, 1,2-bis-(3-ethoxycarbonyl-2-thioureido)-benzene, 1,2-bis-(3-methoxycarbonyl-2-thioureido)-benzene and various other fungicides, e.g., dodecylguanidine acetate, N-dichlorofluoromethylthio-N',N'-dimethyl-N-phenyl-sulfuric acid diamide, 2,5-dimethylfuran-3-carboxylic acid anilide, 2,5-dimethylfuran-3-carboxylic acid cyclohexylamide, 2,5-dimethylfuran-3-carboxylic acid-N-methoxycyclohexylamide, 2-bromobenzoic acid anilide, 2-iodo-benzoic acid anilide, diisopropyl 3-nitroisophthalate, 1-(1,2,4-triazol-1'-yl)-[1-(4'-chlorophenoxy)]-3,3-dimethylbutan-2-one, 1-(1,2,4-triazol-1'-yl)-[1-(4'-chlorophenoxy)]-3,3-dimethylbutan-2-ol, 1-(1-imidazolyl)-2-allyloxy-2-(2,4-dichlorophenyl)-ethane, piperazine-1,4-diyl-bis-1-(2,2,2-trichloroethyl)-formamide, 2,4,5,6-tetrachloro-isophthalonitrile, and 1,2-dimethyl-3,5-diphenyl-pyrazonilium methyl sulfate.

Application may be effected for instance in the form of directly sprayable solutions, powders, suspensions, dispersions, emulsions, oil dispersions, pastes, dusts, broadcasting agents, or granules by spraying, atomizing, dusting, broadcasting or watering. The forms of application depend entirely on the purpose for which the agents are being used; in any case they should ensure a fine distribution of the active ingredient.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethylsulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

There may be added to the compositions or individual active ingredients oils of various types, herbicides, fungicides, nematocides, insecticides, bactericides, trace elements, fertilizers, antifoams (e.g., silicones), growth regulators, antidotes and other herbicidally effective compounds.

The following prior art compounds were used for comparison purposes in the experiments below:

| Active ingredient | |
|---|---|
| A | 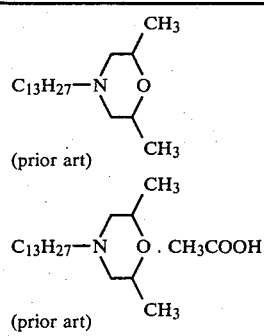 (prior art) |
| B | $C_{13}H_{27}-N\begin{pmatrix}CH_3\\O \cdot CH_3COOH\\CH_3\end{pmatrix}$ (prior art) |
| C | 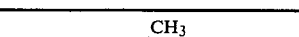 (prior art) |

EXAMPLE 3

Leaves of pot-grown wheat seedlings of the "Jubilar" variety are sprayed with aqueous emulsions containing of 80% (by weight) of active ingredient and 20% of emulsifier, and dusted, after the sprayed-on layer has dried, with spores of wheat mildew (Erysiphe graminus var. tritici). The plants are then placed in a greenhouse at 20° to 22° C. and 75 to 80% relative humidity. The extent of mildew spread is determined after 10 days.

| Active ingredient | Leaf attack after spraying with liquor containing active ingredient in amounts of | | | |
|---|---|---|---|---|
| | 0.006% | 0.012% | 0.025% | 0.05% |
| 1 | | 0 | 0 | 0 |
| 2 | 0 | 0 | 0 | 0 |
| 10 | 0 | 0 | 0 | 0 |
| 8 | 1 | 0 | 0 | 0 |
| 15 | 1 | 0 | 0 | 0 |
| A ⎫ | 3–4 | 3 | 2 | 1 |
| B ⎬ prior art | 4 | 4 | 2 | 1 |
| C ⎭ | 2 | 1 | 1 | 0 |
| Control (untreated) | 4 | | | |

0 = no attack, graduated down to 5 = total attack

EXAMPLE 4

In a further experiment, leaves of pot-grown barley seedlings of the "Firlbecks Union" variety are treated as described in Example 3, and dusted with spores of barley mildew (Erysiphe graminis vari. hordei).

| Active ingredient | Leaf attack after spraying with liquor containing active ingredient in amounts of | | |
|---|---|---|---|
| | 0.006% | 0.012% | 0.025% |
| 1 | 0 | 0 | 0 |
| 2 | 0 | 0 | 0 |
| 10 | 0 | 0 | 0 |
| 8 | 0 | 0 | 0 |
| 15 | 0 | 0 | 0 |
| A ⎫ | 2 | 1 | 0–1 |
| B ⎬ prior art | 3 | 1 | 1 |
| C ⎭ | 1 | 0 | 0 |
| Control (untreated) | 4 | | |

0 = no attack, graduated down to 5 = total attack

EXAMPLE 5

Leaves of pot-grown wheat plants are artificially infected with spores of leaf rust (Puccinia recondita), and the plants are placed for 48 hours in a steam-saturated chamber at from 20° to 25° C. The plants are then sprayed with aqueous liquors containing, as a solution or emulsion in the water, a mixture made up of 80% of active ingredient and 20% of sodium lignin sulfonate, and are set up in a greenhouse at from 20° to 22° C. and 75 to 80% relative humidity. The extent of fungus spread is assessed after 10 days.

| Active ingredient | | Leaf attack after spraying with liquor containing active ingredient in amounts of | | | |
|---|---|---|---|---|---|
| | | 0.012% | 0.025% | 0.05% | 0.1% |
| 1 | | 1 | 1 | 0 | 0 |
| 2 | | 0 | 0 | 0 | 0 |
| 10 | | 0 | 0 | 0 | 0 |
| 8 | | 0 | 0 | 0 | 0 |
| 15 | | 0 | 0 | 0 | 0 |
| A | prior art | 4 | 4 | 3 | 2 |
| B | | 4 | 4 | 4 | 3 |
| C | | 4 | 4 | 3 | 3 |
| Control (untreated) | | 4 | | | |

0 = no attack, graduated down to 5 = total attack

EXAMPLE 6

90 parts by weight of compound 10 is mixed with 10 parts by weight of N-methyl-α-pyrrolidone. A mixture is obtained which is suitable for application in the form of very fine drops.

EXAMPLE 7

20 parts by weight of compound 15 is dissolved in a mixture consisting of 80 parts by weight of xylene, 10 parts by weight of the adduct of 8 to 10 moles of ethylene oxide to 1 mole of oleic acid-N-monoethanolamide, 5 parts by weight of the calcium salt of dodecylbenzenesulfonic acid, and 5 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 8

20 parts by weight of compound 10 is dissolved in a mixture consisting of 40 parts by weight of cyclohexanone, 30 parts by weight of isobutanol, 20 parts by weight of the adduct of 7 moles of ethylene oxide to 1 mole of isooctylphenol, and 10 parts by weight of the adduct of 40 moles of ethylene oxide to 1 mole of castor oil. By pouring the solution into 100,000 parts by weight of water and finely distributing it therein, an aqueous dispersion is obtained containing 0.02% by weight of the active ingredient.

EXAMPLE 9

20 parts by weight of compound 8 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 10

20 parts by weight of compound 15 is well mixed with 3 parts by weight of the sodium salt of diisobutyl-naphthalene-α-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in 20,000 parts by weight of water, a spray liquor is obtained containing 0.1% by weight of the active ingredient.

EXAMPLE 11

3 parts by weight of compound 10 is intimately mixed with 97 parts by weight of particulate kaolin. A dust is obtained containing 3% by weight of the active ingredient.

EXAMPLE 12

30 parts by weight of compound 15 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

EXAMPLE 13

40 parts by weight of compound 10 is intimately mixed with 10 parts of the sodium salt of a phenolsulfonic acid-urea-formaldehyde condensate, 2 parts of silica gel and 48 parts of water. Dilution in 100,000 parts by weight of water gives an aqueous dispersion containing 0.04 wt% of active ingredient.

EXAMPLE 14

20 parts of compound 15 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

We claim:
1. N-arylpropyl-substituted cyclic amines of the formula

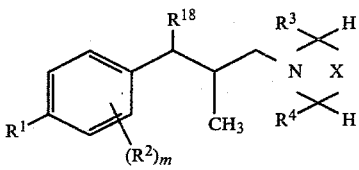

where $R^1$ is tertiary butyl, $R^2$ is chlorine, m denotes the integer 1, $R^3$ and $R^4$ are hydrogen, X denotes

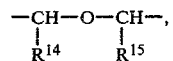

$R^{14}$ and $R^{15}$ being methyl, and $R^{18}$ denotes hydrogen, and salts thereof.

2. A compound as set forth in claim 1 wherein the cyclic amine is N-(3-p-tert-butyl-o-chlorophenyl-2-methyl-1-propyl)-2,6-cis-dimethylmorpholine.

* * * * *